(12) United States Patent
Hibino et al.

(10) Patent No.: US 6,861,566 B2
(45) Date of Patent: Mar. 1, 2005

(54) PROCESS FOR PRODUCING 1-CHLORO-4-ARYLBUTANE

(75) Inventors: Hiroaki Hibino, Oita (JP); Susumu Ohtsuka, Ibaraki (JP); Yasunobu Miyamoto, Toyonaka (JP); Itsuo Okumoto, Sakai-gun (JP)

(73) Assignees: Sumitomo Chemical Company, Limited, Osaka (JP); Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/468,226

(22) PCT Filed: Mar. 11, 2002

(86) PCT No.: PCT/JP02/02240

§ 371 (c)(1),
(2), (4) Date: Aug. 18, 2003

(87) PCT Pub. No.: WO02/072512

PCT Pub. Date: Sep. 19, 2002

(65) Prior Publication Data

US 2004/0097763 A1 May 20, 2004

(30) Foreign Application Priority Data

Mar. 12, 2001 (JP) ............................................. 2001-68337

(51) Int. Cl.$^7$ .......................... C07C 17/00; C07C 22/00; C07C 25/00
(52) U.S. Cl. ................. 570/191; 570/190; 570/192; 570/193; 570/194; 570/257; 570/261
(58) Field of Search ............................... 570/190, 191, 570/192, 193, 194, 257, 261

(56) References Cited

U.S. PATENT DOCUMENTS 4,272,454 A   6/1981   Maggi et al.

OTHER PUBLICATIONS

Chemical Abstracts, vol. 77, No. 13, (1972), p. 352, the abstract No. 87716z, Kruglova, N. V. & Friedlina, R. Kh., Izv. Akad. Nauk SSSR, Ser. Khim. No. 4, (1972), pp. 886–890.

J. Agric. Food Chem., vol. 38, No. 10, 1990, pp. 1965–1971.

J. Org. Chem., vol. 43, No. 21, 1978, pp. 4120–4125.

*Primary Examiner*—Elvis O. Price
(74) *Attorney, Agent, or Firm*—Birch, Stewart, Kolasch & Birch, LLP

(57) ABSTRACT

There is provided an industrially advantageous process for producing a 1-chloro-4-arylbutane represented by the general formula (2):

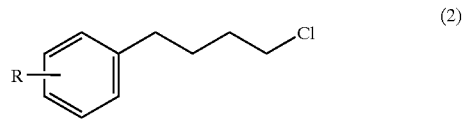

(2)

wherein R represents hydrogen, lower alkyl, or lower alkoxy, characterized by reacting 1-bromo-3-chloropropane with a compound represented by the general formula (1):

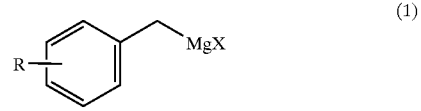

(1)

wherein R is as defined above; and X represents chlorine, bromine, or iodine, in a solvent.

10 Claims, No Drawings

PROCESS FOR PRODUCING 1-CHLORO-4-ARYLBUTANE

This application is the national phase under 35 U.S.C. §371 of PCT International Application No. PCT/JP02/02240 which has an International filing date of Mar. 11, 2002, which designated the United States of America.

TECHNICAL FIELD

The present invention relates to a process for producing a 1-chloro-4-arylbutane.

BACKGROUND ART

A 1-chloro-4-arylbutane represented by the general formula (2):

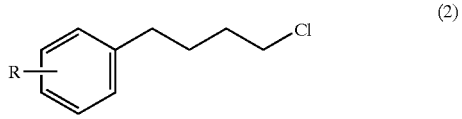

(2)

wherein R represents a hydrogen atom, a lower alkyl group, or a lower alkoxy group is useful as an intermediate for synthesizing medicaments and agrochemicals, and the reaction of a 4-aryl-1-butanol with thionyl chloride is generally employed as its production process. However, such a process is not always an industrially satisfactory production process because the production of the starting material, a 4-aryl-1-butanol, is troublesome and further the process requires plural steps.

DISCLOSURE OF INVENTION

Under these circumstances, the present inventors have studies a more industrially advantageous process for producing a 1-chloro-4-arylbutane, and have found that a 1-chloro-4-arylbutane can be obtained by one step in a good yield by reacting 1-bromo-3-chloropropane, which is inexpensive and easily available, with a benzylmagnesium halide in a solvent to attain the present invention.

That is, the present invention is to provide a process for producing a 1-chloro-4-arylbutane represented by the general formula (2):

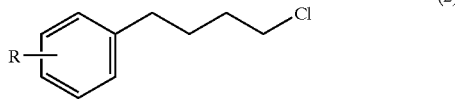

(2)

wherein R represents a hydrogen atom, a lower alkyl group, or a lower alkoxy group, which comprises reacting 1-bromo-3-chloropropane with a compound represented by the general formula (1):

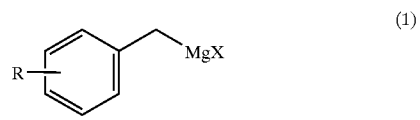

(1)

wherein R is as defined above; and X represents a chlorine atom, a bromine atom, or an iodine atom, in a solvent.

MODE FOR CARRYING OUT THE INVENTION

Hereinafter, the present invention will be illustrated in detail.

In the compound represented by the general formula (1):

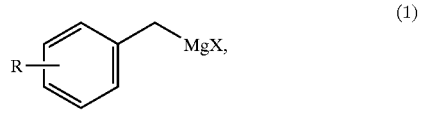

(1)

(hereinafter abbreviated to the compound (1)), R represents a hydrogen atom, a lower alkyl group, or a lower alkoxy group. Further, X in the above compound (1) represents a chlorine atom, a bromine atom, or an iodine atom.

Examples of the lower alkyl group include an alkyl group having 1 to 6 carbon atoms such as methyl group, ethyl group, n-propyl group, isopropyl group, n-butyl group, isobutyl group, sec-butyl group, tert-butyl group, n-heptyl group, n-hexyl group, etc. Examples of the lower alkoxy group include an alkoxy group having 1 to 6 carbon atoms such as methoxy group, ethoxy group, n-propoxy group, isopropoxy group, n-butoxy group, isobutoxy group, sec-butoxy group, tert-butoxy group, n-heptyloxy group, n-hexyloxy group, etc.

Examples of the compound (1) include benzylmagnesium chloride, benzylmagnesium bromide, benzylmagnesium iodide, 2-methylbenzylmagnesium chloride, 2-methylbenzylmagnesium bromide, 2-methylbenzylmagnesium iodide, 3-methylbenzylmagnesium chloride, 3-methylbenzylmagnesium bromide, 3-methylbenzylmagnesium iodide, 4-methylbenzylmagnesium chloride, 4-methylbenzylmagnesium bromide, 4-methylbenzylmagnesium iodide, 2-ethylbenzylmagnesium chloride, 2-ethylbenzylmagnesium bromide, 2-ethylbenzylmagnesium iodide, 3-n-propylbenzylmagnesium chloride, 3-n-propylbenzylmagnesium bromide, 3-n-propylbenzylmagnesium iodide, 2-isopropylbenzylmagnesium chloride, 2-isopropylbenzylmagnesium bromide, 2-isopropylbenzylmagnesium iodide, 3-n-butylbenzylmagnesium chloride, 3-n-butylbenzylmagnesium bromide, 3-butylbenzylmagnesium iodide, 2-tert-butylbenzylmagnesium chloride, 2-tert-butylbenzylmagnesium bromide, 2-tert-butylbenzylmagnesium iodide, 2-methoxybenzylmagnesium chloride, 2-methoxybenzylmagnesium bromide, 2-methoxybenzylmagnesium iodide, 3-methoxybenzylmagnesium chloride, 3-methoxybenzylmagensium bromide, 3-methoxybenzylmagnesium iodide, 4-methoxybenzylmagnesium chloride, 4-methoxybenzylmagnesium bromide, 4-methoxybenzylmagnesium iodide, 2-ethoxybenzylmagnesium chloride, 2-ethoxybenzylmagnesium bromide, 2-ethoxybenzylmagnesium iodide, 3-n-propoxybenzylmagnesium chloride, 3-n-propoxybenzylmagnesium bromide, 3-n-propoxybenzylmagnesium iodide, 2-isopropoxybenzylmagnesium chloride, 2-isopropoxybenzylmagnesium bromide, 2-isopropoxybenzylmagnesium iodide, 3-n-butoxybenzylmagnesium chloride, 3-n-butoxybenzylmagnesium bromide, 3-n-butoxybenzylmagnesium iodide, 2-isobutoxybenzylmagnesium chloride, 2-isobutoxybenzylmagnesium bromide, 2-isobutoxybenzylmagensium iodide, etc.

The compound (1) to be used may be a commercially available product. Alternatively, there may be used, for example, a product obtained by reacting magnesium with a benzyl halide in a solvent as described hereinafter. It is preferred to use the benzyl halide and the solvent which have been subjected to dehydration treatment with a dehydrating agent, for example, molecular sieves, magnesium sulfate, etc., or have been dehydrated by distillation.

The process of the present invention is the reaction of 1-bromo-3-chloropropane with the compound (1) in a solvent.

In this reaction, the compound (1) may be used in an amount of once or more by the mole based on 1-bromo-3-chloropropane, or 1-bromo-3-chloropropane may be used in an amount of once or more by the mole based on the compound (1). The amount may be appropriately chosen by taking into account the reactivity, economical efficiency, etc.

Examples of the solvent include ethereal solvents such as diethyl ether, diisopropyl ether, di-n-butyl ether, diisobutyl ether, methyl-tert-butyl ether, tetrahydrofuran, dimethoxyethane, anisole, etc.; mixed solvents of these ethereal solvents and aromatic hydrocarbon solvents such as toluene, xylene, etc.; mixed solvents of these ethereal solvents and aliphatic hydrocarbon solvents such as hexane, heptane, etc.; and the like. Usually, the solvent is used after subjecting it to dehydration treatment with a dehydrating agent such as molecular sieves, etc., or to dehydration treatment by distillation.

The amount of the solvent to be used is usually twice or more by weight based on the compound (1). The upper limit is not specifically limited but, from the practical viewpoint, it is 20 times or less by weight because too much of the solvent is disadvantageous to the volumetric efficiency. In case of using as the compound (1) its solution in the solvent, further addition of the solvent may not be required.

The reaction temperature of the above-described reaction is usually −60 to 100° C., preferably −20 to 60° C.

In the above-described reaction, 1-bromo-3-chloropropane may be added to a mixture of the compound (1) and the solvent, or the compound (1) may be added to a mixture of 1-bromo-3-chloropropane and the solvent. Alternatively, both the compound (1) and 1-bromo-3-chloropropane together may be poured into the solvent.

After completion of the reaction, the resultant reaction mixture can be subjected to decomposition treatment of the remaining compound (1) by mixing it with, for example, hydrochloric acid, sulfuric acid, an acidic aqueous solution of ammonium chloride, etc., water, or the like, followed by subjecting to separation treatment to isolate the desired 1-chloro-4-arylbutane represented by the general formula (2):

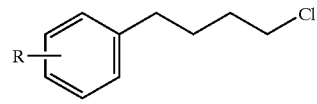

(2)

wherein R is as defined above. The 1-chloro-4-arylbutane represented by the general formula (2) thus isolated may be further purified by, for example, distillation, column chromatography and the like.

Upon subjecting to the above decomposition treatment of the remaining compound (1) or the subsequent separation treatment, a water immiscible organic solvent may be added. Examples of the water immiscible organic solvent include aromatic hydrocarbon solvents such as toluene, xylene, etc.; aliphatic hydrocarbon solvents such as hexane, heptane, etc.; halogenated hydrocarbon solvents such as dichloromethane, chlorobenzene, etc. The amount thereof to be used is not specifically limited.

Examples of the 1-chloro-4-arylbutane represented by the general formula (2) thus obtained include 1-chloro-4-phenylbutane, 1-chloro-4-(2-methylphenyl)butane, 1-chloro-4-(3-methylphenyl)butane, 1-chloro-4-(4-methylphenyl)butane, 1-chloro-4-(2-ethylphenyl)butane, 1-chloro-4-(3-n-propylphenyl)butane, 1-chloro-4-(2-isopropylphenyl)butane, 1-chloro-4-(3-n-butylphenyl)butane, 1-chloro-4-(2-tert-butylphenyl)butane, 1-chloro-4-(2-methoxyphenyl)butane, 1-chloro-4-(3-methoxyphenyl)butane, 1-chloro-4-(4-methoxyphenyl)butane, 1-chloro-4-(2-ethoxyphenyl)butane, 1-chloro-4-(3-n-propoxyphenyl)butane, 1-chloro-4-(2-isopropoxyphenyl)butane, 1-chloro-4-(3-n-butoxyphenyl)butane, 1-chloro-4-(2-isobutoxyphenyl)butane, etc.

EXAMPLES

Hereinafter, the present invention will be further illustrated in detail by means of Examples but the present invention is not limited to these Examples.

Example 1

Benzylmagnesium chloride/tetrahydrofuran solution (content: 12.5% by weight) (150 g) was placed in a reaction vessel equipped with a stirrer and a condenser and the inner temperature was adjusted to 0° C. At the same temperature, 1-bromo-3-chloropropane (19.6 g) was added dropwise over 2 hours, followed by stirring and maintaining at the inner temperature of 0 to 5° C. for 4 hours. The reaction mixture was added to 10% by weight hydrochloric acid (55 g) (at this time, the inner temperature of the mixture was maintained at 30° C. or lower). After stirring and allowing to stand, an organic layer was separated and the organic layer was washed with saturated saline (55 g) and concentrated under reduced pressure to obtain an oily product (23.2 g) containing 1-chloro-4-phenylbutane. When this was analyzed by gas chromatography (Internal standard method), the content of 1-chloro-4-phenylbutane was 89.5% by weight. Yield based on 1-bromo-3-chloropropane: 98.6%.

Example 2

In a reaction vessel equipped with a stirrer and a condenser, 1-bromo-3-chloropropane (21.5 g) and tetrahydrofuran (123 g) were placed and the inner temperature was adjusted to 0° C. At the same temperature, benzylmagnesium chloride/tetrahydrofuran solution (content: 13.7% by weight) (150 g) was added dropwise over 2 hours, followed by stirring and maintaining at the inner temperature of 0 to 5° C. for 4 hours. The reaction mixture was added to 10% by weight hydrochloric acid (60 g) (at this time, the inner temperature of the mixture was maintained at 30° C. or lower). After stirring and allowing to stand, an organic layer was separated and the organic layer was washed with saturated saline (60 g) and concentrated under reduced pressure to obtain an oily product (23.6 g) containing 1-chloro-4-phenylbutane. When this was analyzed by gas chromatography (Internal standard method), the content of 1-chloro-4-phenylbutane was 91.0% by weight. Yield based on 1-bromo-3-chloropropane: 94.1%.

INDUSTRIAL APPLICABILITY

According to the process of the present invention, the desired 1-chloro-4-arylbutane can be produced by one step in a good yield by reacting 1-bromo-3-chloropropane, which is inexpensive and easily available, with a benzylmagnesium halide. Therefore, the process of the present invention is an industrially advantageous process.

What is claimed is:

1. A process for producing a 1-chloro-4-arylbutane represented by the general formula (2):

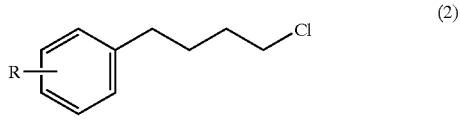

wherein R represents a hydrogen atom, a lower alkyl group, or a lower alkoxy group, which comprises reacting 1-bromo-3-chloropropane with a compound represented by the general formula (1):

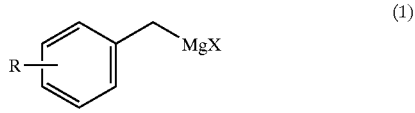

wherein R is as defined above; and X represents a chlorine atom, a bromine atom, or an iodine atom, in a solvent.

2. A process according to claim 1, wherein the solvent is selected from ethereal solvents, mixed solvents of ethereal solvents and aromatic hydrocarbon solvents, and mixed solvents of ethereal solvents and aliphatic hydrocarbon solvents.

3. A process according to claim 1 or 2, wherein the solvent is an ethereal solvent selected from diethyl ether, diisopropyl ether, di-n-butyl ether, diisobutyl ether, methyl-tert-butyl ether, tetrahydrofuran, dimethoxyethane and anisole, or a mixed solvent of said ethereal solvent and toluene, xylene, hexane or heptane.

4. A process according to claim 1, wherein the amount by weight of solvent used is 2 to 20 times the amount by weight of the compound of formula (1).

5. A process according to claim 1, wherein the reaction temperature is −60 to 100° C.

6. A process according to claims 1, which further comprises, after completion of the reaction, subjecting the resultant reaction mixture to decomposition treatment of the remaining compound of formula (1) by mixing it with hydrochloric acid, sulfuric acid, an acidic aqueous solution of ammonium chloride, or water, followed by subjecting to separation treatment to isolate the compound of formula (2).

7. A process according to claim 6, wherein a water immiscible organic solvent is added upon subjecting the reaction mixture to decomposition treatment of the remaining compound of formula (1) or the subsequent separation treatment.

8. A process according to claim 7, wherein the water immiscible organic solvent is an aromatic hydrocarbon solvent, an aliphatic hydrocarbon solvent, or an halogenated hydrocarbon solvent.

9. A process according to claim 1, wherein the compound of Formula (1) is benzylmagnesium chloride.

10. A process according to claim 1, wherein the compound of formula (2) is 1-chloro-4-phenylbutane.

* * * * *